United States Patent
Pflueger

(10) Patent No.: US 7,591,790 B2
(45) Date of Patent: *Sep. 22, 2009

(54) MICRO-INVASIVE DEVICE

(75) Inventor: D. Russell Pflueger, San Juan Capistrano, CA (US)

(73) Assignee: Stryker Puerto Rico Limited, Arroyo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/888,321

(22) Filed: Jul. 30, 2007

(65) Prior Publication Data

US 2008/0064984 A1 Mar. 13, 2008

Related U.S. Application Data

(63) Continuation of application No. 10/667,768, filed on Sep. 22, 2003, which is a continuation of application No. 10/093,765, filed on Mar. 8, 2002.

(60) Provisional application No. 60/278,128, filed on Mar. 23, 2001, provisional application No. 60/281,848, filed on Apr. 5, 2001, provisional application No. 60/305,178, filed on Jul. 13, 2001, provisional application No. 60/322,909, filed on Sep. 17, 2001, provisional application No. 60/342,436, filed on Dec. 21, 2001.

(51) Int. Cl.
*A61B 10/00* (2006.01)

(52) U.S. Cl. ..................................... 600/568

(58) Field of Classification Search ......... 600/562–570; 606/80, 185, 170, 172, 102, 167, 180; 604/35, 604/164.01–164.13, 187, 218, 27, 540, 151, 604/131; 415/73; 29/889

See application file for complete search history.

(56) References Cited

U.S. PATENT DOCUMENTS 1,493,240 A 5/1924 Bohn (Continued)

FOREIGN PATENT DOCUMENTS

EP 0 190 000 8/1986

(Continued)

OTHER PUBLICATIONS

USPTO Office Action dated Jul. 3, 2002, U.S. Appl. No. 10/093,765, filed Mar. 8, 2002, now U.S. Patent No. 6,673,023.

(Continued)

*Primary Examiner*—Max Hindenburg
*Assistant Examiner*—Brian Szmal
(74) *Attorney, Agent, or Firm*—Stout, Uxa, Buyan & Mullins, LLP; Frank J. Uxa

(57) ABSTRACT

An apparatus for removing tissue and/or other material from a patient, particularly a breast of a patient, is provided. The apparatus generally includes a handpiece and a tissue removal mechanism connected thereto. The tissue removal mechanism includes a cannula having an open distal tip and an outer diameter of less than about 5 mm, or less than about 2 mm. The mechanism further includes a rotatable element having a distal portion with helical threading. The distal portion of the rotatable element extends beyond the open distal tip of the cannula in order to allow tissue to prolapse between turns of the helical threading. The apparatus is designed to draw soft tissue into the cannula upon rotation of the rotatable element and without the need for supplemental sources of aspiration.

17 Claims, 3 Drawing Sheets

U.S. PATENT DOCUMENTS

| | | | |
|---|---|---|---|
| 2,526,662 A | 10/1950 | Hipps et al. |
| 2,532,370 A | 12/1950 | Perrill |
| 3,308,828 A | 3/1967 | Pippin |
| 3,477,423 A | 11/1969 | Griffith |
| 3,550,583 A | 12/1970 | Chiku |
| 3,553,625 A | 1/1971 | Stedman |
| 3,590,808 A | 7/1971 | Muller |
| 3,710,781 A | 1/1973 | Hutchins, IV et al. |
| 3,732,858 A | 5/1973 | Banko |
| 3,735,751 A | 5/1973 | Katz |
| 3,938,379 A | 2/1976 | Bingham |
| 4,023,562 A | 5/1977 | Hynecek et al. |
| 4,061,146 A | 12/1977 | Baehr et al. |
| 4,167,944 A | 9/1979 | Banko |
| 4,210,029 A | 7/1980 | Porter |
| 4,274,423 A | 6/1981 | Mizuno et al. |
| 4,306,570 A | 12/1981 | Matthews |
| 4,371,342 A | 2/1983 | Filhol |
| 4,393,878 A | 7/1983 | Kahn |
| 4,461,305 A | 7/1984 | Cibley |
| 4,512,344 A | 4/1985 | Barber |
| 4,600,014 A | 7/1986 | Beraha |
| 4,649,919 A | 3/1987 | Thimsen et al. |
| 4,699,154 A | 10/1987 | Lindgren |
| 4,722,348 A | 2/1988 | Ligtenberg et al. |
| 4,844,064 A | 7/1989 | Thimsen et al. |
| 4,857,046 A | 8/1989 | Stevens et al. |
| 4,878,898 A | 11/1989 | Griffin et al. |
| 4,883,458 A | 11/1989 | Shiber |
| 4,901,731 A | 2/1990 | Millar |
| 4,919,146 A * | 4/1990 | Rhinehart et al. ........... 600/565 |
| 4,924,877 A | 5/1990 | Brooks |
| RE33,258 E | 7/1990 | Onik et al. |
| 4,958,625 A | 9/1990 | Bates et al. |
| 4,979,939 A | 12/1990 | Shiber |
| 5,002,553 A | 3/1991 | Shiber |
| 5,018,529 A | 5/1991 | Tenerz et al. |
| 5,067,491 A | 11/1991 | Taylor, II et al. |
| 5,074,841 A | 12/1991 | Ademovic et al. |
| 5,084,052 A | 1/1992 | Jacobs |
| 5,085,223 A | 2/1992 | Lars et al. |
| 5,113,868 A | 5/1992 | Wise et al. |
| RE34,056 E | 9/1992 | Lindgren et al. |
| 5,183,054 A | 2/1993 | Burkholder et al. |
| 5,195,375 A | 3/1993 | Tenerz et al. |
| 5,207,102 A | 5/1993 | Takahashi et al. |
| 5,226,423 A | 7/1993 | Tenerz et al. |
| 5,234,000 A | 8/1993 | Hakky et al. |
| 5,238,004 A | 8/1993 | Sahatjian et al. |
| 5,269,785 A | 12/1993 | Bonutti |
| 5,290,303 A | 3/1994 | Pingleton et al. |
| 5,313,957 A | 5/1994 | Little |
| 5,320,627 A | 6/1994 | Sorensen et al. |
| 5,327,905 A | 7/1994 | Avitall |
| 5,373,852 A | 12/1994 | Harrison et al. |
| 5,383,884 A | 1/1995 | Summers |
| 5,412,994 A | 5/1995 | Cook et al. |
| 5,423,799 A | 6/1995 | Shiu |
| 5,433,216 A | 7/1995 | Sugrue et al. |
| 5,433,739 A | 7/1995 | Sluijter et al. |
| 5,450,853 A | 9/1995 | Hastings et al. |
| 5,474,086 A | 12/1995 | McCormick et al. |
| 5,526,822 A | 6/1996 | Burbank et al. |
| 5,569,178 A | 10/1996 | Henley |
| 5,569,284 A | 10/1996 | Young et al. |
| 5,571,147 A | 11/1996 | Sluijter et al. |
| 5,591,187 A | 1/1997 | Dekel |
| 5,618,296 A | 4/1997 | Sorensen et al. |
| 5,619,993 A | 4/1997 | Lee |
| 5,628,748 A | 5/1997 | Vicari |
| 5,637,076 A | 6/1997 | Hazard et al. |
| 5,643,303 A | 7/1997 | Donahue |
| 5,662,122 A | 9/1997 | Evans |
| 5,669,926 A | 9/1997 | Aust et al. |
| 5,681,282 A | 10/1997 | Eggers et al. |
| 5,685,840 A | 11/1997 | Schechter et al. |
| 5,693,011 A | 12/1997 | Onik |
| 5,694,946 A | 12/1997 | Tenerz et al. |
| 5,715,827 A | 2/1998 | Corl et al. |
| 5,722,401 A | 3/1998 | Pietroski et al. |
| 5,741,287 A | 4/1998 | Alden et al. |
| 5,759,185 A | 6/1998 | Grinberg |
| 5,762,073 A | 6/1998 | Choy |
| 5,766,194 A | 6/1998 | Smith |
| 5,772,627 A | 6/1998 | Acosta et al. |
| 5,785,705 A | 7/1998 | Baker |
| 5,807,265 A | 9/1998 | Itoigawa |
| 5,826,576 A | 10/1998 | West |
| 5,836,886 A | 11/1998 | Itoigawa |
| 5,843,019 A | 12/1998 | Eggers et al. |
| 5,857,995 A | 1/1999 | Thomas et al. |
| 5,876,414 A | 3/1999 | Straub |
| 5,902,248 A | 5/1999 | Millar et al. |
| 5,908,446 A | 6/1999 | Imran |
| 5,913,857 A | 6/1999 | Ritchart et al. |
| 5,916,175 A | 6/1999 | Bauer |
| 5,916,229 A | 6/1999 | Evans |
| 5,925,056 A | 7/1999 | Thomas et al. |
| 5,935,131 A | 8/1999 | Bonutti |
| 5,968,062 A | 10/1999 | Thomas et al. |
| 5,976,105 A | 11/1999 | Marcove et al. |
| 5,976,164 A | 11/1999 | Bencini et al. |
| 5,980,504 A | 11/1999 | Sharkey et al. |
| 5,997,536 A | 12/1999 | Osswald et al. |
| 6,000,399 A | 12/1999 | Choy |
| 6,001,112 A | 12/1999 | Taylor |
| 6,007,570 A | 12/1999 | Sharkey et al. |
| 6,017,316 A | 1/2000 | Richart et al. |
| 6,019,728 A | 2/2000 | Iwata et al. |
| 6,019,729 A | 2/2000 | Itoigawa et al. |
| 6,022,354 A | 2/2000 | Mercuri et al. |
| 6,036,681 A | 3/2000 | Hooven |
| 6,045,532 A | 4/2000 | Eggers et al. |
| 6,066,153 A | 5/2000 | Lev |
| 6,071,284 A | 6/2000 | Fox |
| 6,073,051 A | 6/2000 | Sharkey et al. |
| 6,077,230 A | 6/2000 | Gregoire et al. |
| 6,083,179 A | 7/2000 | Oredsson |
| 6,083,237 A | 7/2000 | Huitema et al. |
| 6,086,543 A | 7/2000 | Anderson et al. |
| 6,095,149 A | 8/2000 | Sharkey et al. |
| 6,099,514 A | 8/2000 | Sharkey et al. |
| 6,120,457 A | 9/2000 | Coombes et al. |
| 6,122,549 A | 9/2000 | Sharkey et al. |
| 6,126,682 A | 10/2000 | Sharkey et al. |
| 6,129,713 A | 10/2000 | Mangosong et al. |
| 6,136,014 A | 10/2000 | Sirimanne et al. |
| 6,142,955 A | 11/2000 | Farascioni et al. |
| 6,156,046 A | 12/2000 | Passafaro et al. |
| 6,162,214 A | 12/2000 | Mueller et al. |
| 6,168,593 B1 | 1/2001 | Sharkey et al. |
| 6,174,313 B1 | 1/2001 | Bonutti |
| 6,190,381 B1 | 2/2001 | Olsen et al. |
| 6,203,542 B1 | 3/2001 | Ellsberry et al. |
| 6,231,522 B1 | 5/2001 | Voegele et al. |
| 6,245,028 B1 | 6/2001 | Furst et al. |
| 6,254,553 B1 | 7/2001 | Lidgren et al. |
| 6,264,611 B1 | 7/2001 | Ishikawa et al. |
| 6,273,861 B1 | 8/2001 | Bates et al. |
| 6,296,608 B1 | 10/2001 | Daniels et al. |
| 6,309,345 B1 | 10/2001 | Stelzer et al. |
| 6,311,562 B1 | 11/2001 | Hanada |
| 6,325,806 B1 | 12/2001 | Fox |
| 6,554,799 B1 | 4/2003 | Hatamura et al. |

| | | | |
|---|---|---|---|
| 6,673,023 B2 | 1/2004 | Pflueger | |
| 6,783,532 B2 | 8/2004 | Steiner et al. | |
| 6,846,314 B2 | 1/2005 | Shapira | |

FOREIGN PATENT DOCUMENTS

| | | |
|---|---|---|
| GB | 2111390 | 7/1983 |
| IT | 1246197 | 11/1994 |
| JP | 2000-287985 | 10/2000 |
| WO | WO 94/24941 | 11/1994 |
| WO | WO 00/56208 | 9/2000 |

OTHER PUBLICATIONS

USPTO Office Action dated Dec. 31, 2002, U.S. Appl. No. 10/093,765, filed Mar. 8, 2002, now U.S. Patent No. 6,673,023.
USPTO Office Action dated Feb. 2, 2006, U.S. Appl. No. 10/667,768, filed Sep. 22, 2003.
USPTO Office Action dated Aug. 16, 2006, U.S. Appl. No. 10/667,768, filed Sep. 22, 2003.
USPTO Office Action dated Oct. 25, 2006, U.S. Appl. No. 10/667,768, filed Sep. 22, 2003.
USPTO Office Action dated Mar. 28, 2007, U.S. Appl. No. 10/667,768, filed Sep. 22, 2003.
U.S. Appl. No. 10/093,774, filed Mar. 8, 2002.
U.S. Appl. No. 10/093,775, filed Mar. 8, 2002.
USPTO Office Action dated May 28, 2004, U.S. Appl. No. 10/093,775, filed Mar. 8, 2002.
USPTO Office Action dated Nov. 24, 2004, U.S. Appl. No. 10/093,775, filed Mar. 8, 2002.
USPTO Advisory Action dated Feb. 11, 2005, U.S. Appl. No. 10/093,775, filed Mar. 8, 2002.
USPTO Office Action dated Feb. 5, 2004, U.S. Appl. No. 10/093,774, filed Mar. 8, 2002.
USPTO Office Action dated Mar. 15, 2004, U.S. Appl. No. 10/093,774, filed Mar. 8, 2002.
USPTO Office Action dated Sep. 30, 2004, U.S. Appl. No. 10/093,774, filed Mar. 8, 2002.
USPTO Advisory Action dated Dec. 15, 2004, U.S. Appl. No. 10/093,774, filed Mar. 8, 2002.
USPTO Office Action dated Jan. 26, 2005, U.S. Appl. No. 10/093,774, filed Mar. 8, 2002.
USPTO Interview Summary dated Mar. 21, 2005 U.S. Appl. No. 10/093,774, filed Mar. 8, 2002.
USPTO Office Action dated Oct. 4, 2005, U.S. Appl. No. 10/093,774, filed Mar. 8, 2002.
USPTO Interview Summary dated Nov. 15, 2005, U.S. Appl. No. 10/093,774, filed Mar. 8, 2002.
USPTO Office Action dated Jan. 24, 2006, U.S. Appl. No. 10/093,774, filed Mar. 8, 2002.
USPTO Office Action dated Sep. 22, 2006, U.S. Appl. No. 10/093,774, filed Mar. 8, 2002.
Okusa et al, "Micro pump for extrusion of exudate in middle ear", Medical Electronics and Biomedical Engineering, vol. 37 (Apr. 1999), p. 329.
English translation of: Okusa et al, "Micro pump for extrusion of exudate in middle ear", Medical Electronics and Biomedical Engineering, vol. 37 (Apr. 1999), p. 329.
USPTO Advisory Action dated Dec. 10, 2008 in U.S. Appl. No. 11/810,552, filed Jun. 5, 2007.
English Abstract of above-listed Japanese Patent No. JP 2000-287985, published Oct. 17, 2000.
English Translation of above-listed PCT International Publication No. WO 94/24941.
U.S. Appl. No. 11/134,569, filed May 20, 2005.
U.S. Appl. No. 11/810,552, filed Jun. 5, 2007.
"Examiner's Answer" mailed Jan. 16, 2008 in related-parent U.S. Appl. No. 10/093,774, filed Mar. 8, 2002, Before the Board of Patent Appeals and Interferences in response to Appeal Brief filed May 15, 2007.
USPTO Office action dated Jan. 7, 2008 in U.S. Appl. No. 11/810,552, filed Jun. 5, 2007.
USPTO Interview Summary dated Feb. 26, 2008 in U.S. Appl. No. 11/810,552, filed Jun. 5, 2007.
USPTO Interview Summary dated Jun. 4, 2008, in U.S. Appl. No. 11/810,552, filed Jun. 5, 2007.
USPTO Office Action dated Sep. 16, 2008 in U.S. Appl. No. 11/810,552, filed Jun. 5, 2007.
Yotaro Hatamura, "Micro-Manipulation and Micro-Robots", Japan Medical Association Journal (JMAJ), vol. 46, No. 8, pp. 321-326, Aug. 2003.
Iatridis et al., "Alterations in the mechanical behavior of the human lumbar nucleus pulposus with degeneration and aging", Journal of Orthopaedic Research, vol. 15, No. 2, pp. 318-322, 1997.
Britannica Online Encyclopedia, "screw pump", accessed from http://www.britannica.com/EBchecked/topic/529911/screw-pump?view=print on Apr. 10, 2009.
USPTO Office Action dated Apr. 15, 2009 in U.S. Appl. No. 11/810,552, filed Jun. 5, 2007.
Sato et al., "In Vivo Intradiscal Pressure Measurement in Healthy Individuals and in Patients with Ongoing Back Problems", Dept. Of Orthopaedic Surg., Fukushima Med. University, School of Medicine and the Dept. of Orthopaedic Surg., Osaka Med. College, Japan, Dec. 1, 1999.
"Predictive Pressure Controlled Discography", www.spinaldiagnostics.com/predpressure. htm. and www.spinaldiagnostics.com/predtables. htm, Spinal Diagnostics & Treatment Center, Jan. 1999.
Cripton et al., "A Novel Technique for Measuring in Vitro Pressure in Cervical Intervertebral Discs", Dept. of Mech. Eng., Queen's University, Kingstron, Canada, and Müller Inst. for Biomech., University of Bern, Bern, Switzerland, Aug. 14, 1998.
Steffen et al., "Multilocalized Intradiscal Pressure Measurements in the Cadaveric Lumbar Spine", Jun. 1995.
Gudavalli et al., "Funded Basic Sciences Research: What Happens During Distraction Manipulation? Disc Pressure Changes", National College of Chiropractic, Lombard, IL, and Loyala University Chicago, Maywood, IL, Abstract from the Proceedings of the International Society for the Study of the Lumbar Spine, dated 1998.
Choy et al., "B. Fall of Intradiscal Pressure with Laser Ablation", J. Clin. Laser Med. & Surg., vol. 13, No. 3, Mary Ann Liebert, Inc., pp. 149-151, Jun. 1995.
Case et al., "Change of intradisc pressure versus volume change", J. Clin. Laser Med. Surg., vol. 13(3), pp. 143-147, Jun. 1995.
Cripton et al., "A minimally disruptive technique for measuring intervertebral disc pressure in vitro: application to the cervical spine", J. Biomech, vol. 34(4), 545-549, Apr. 2001.
Wilke et al., "New in vivo measurements of pressures in the intervertebral disc in daily life", Spine, vol. 15:24(8), pp. 755-762, Apr. 1999.
McNally et al., "Development and validation of a new transducer for intradiscal pressure measurement", J. Biomed. Eng., vol. 14(6), pp. 495-498, Nov. 1992.
Panjabi et al., "Intrinsic disc pressure as a measurement of integrity of the lumbar spine", Spine, vol. 13(8), pp. 913-917, Aug. 1988.
USPTO Office Action dated Mar. 20, 2009 in U.S. Appl. No. 11/134,569, filed May 20, 2005.

* cited by examiner

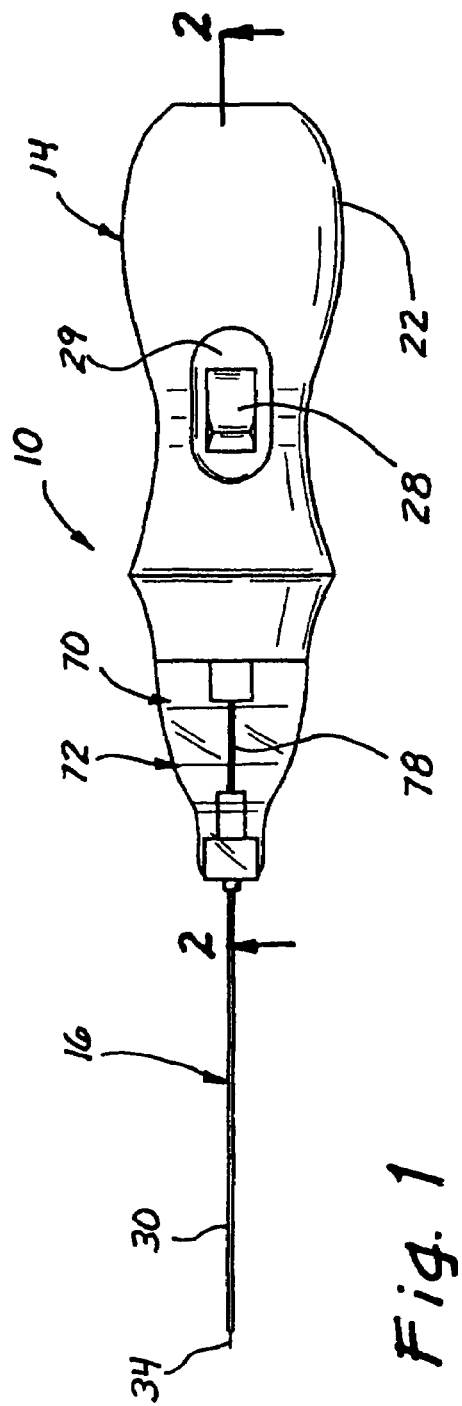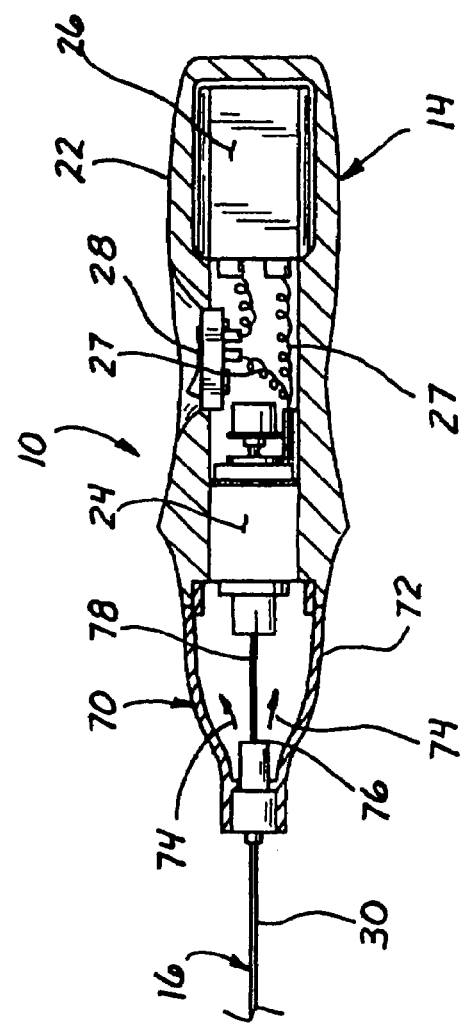

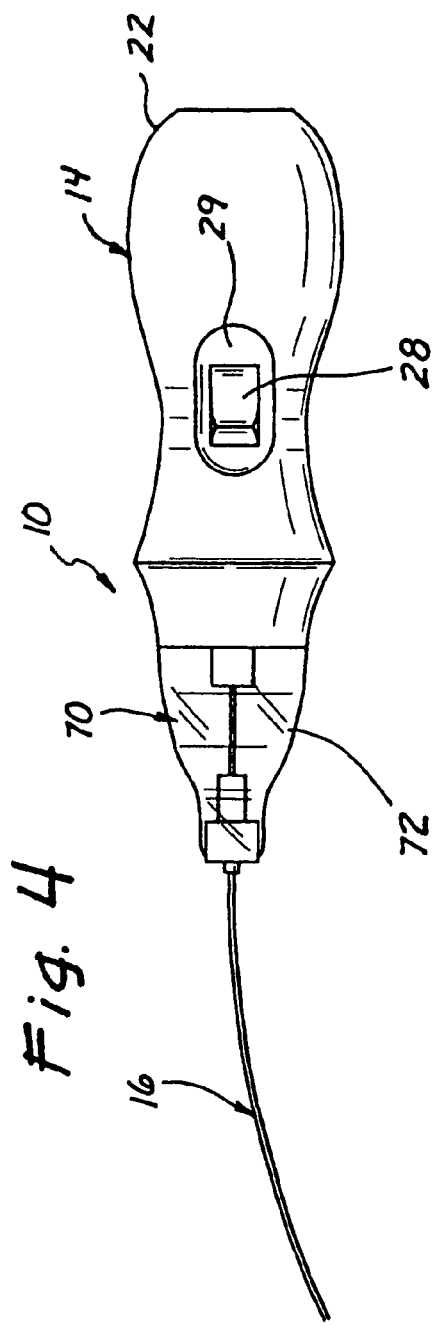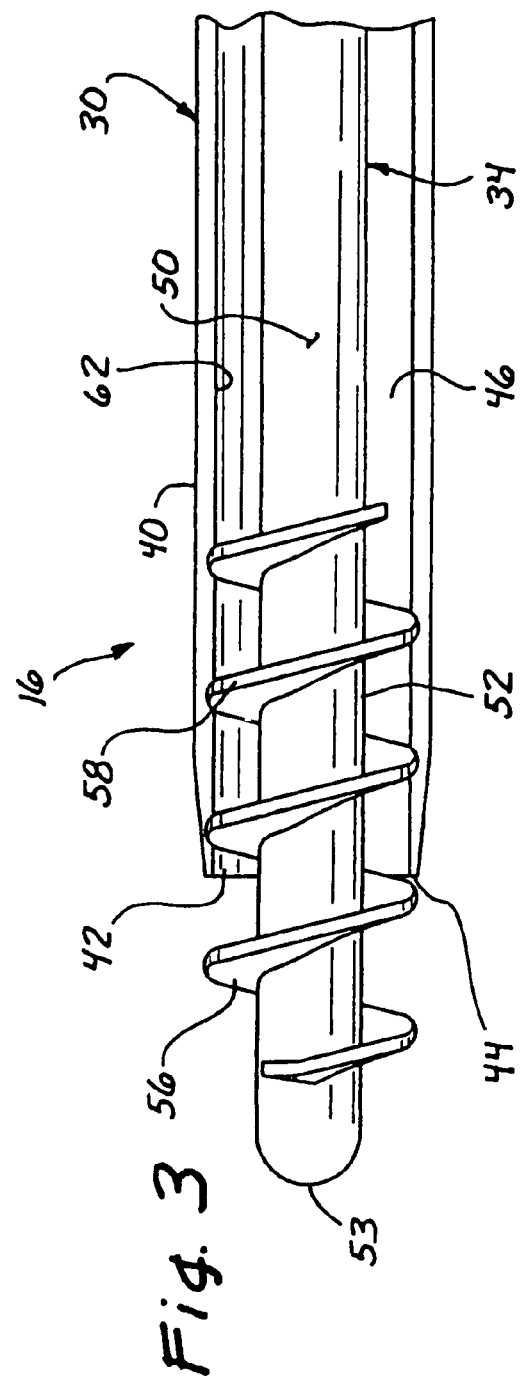

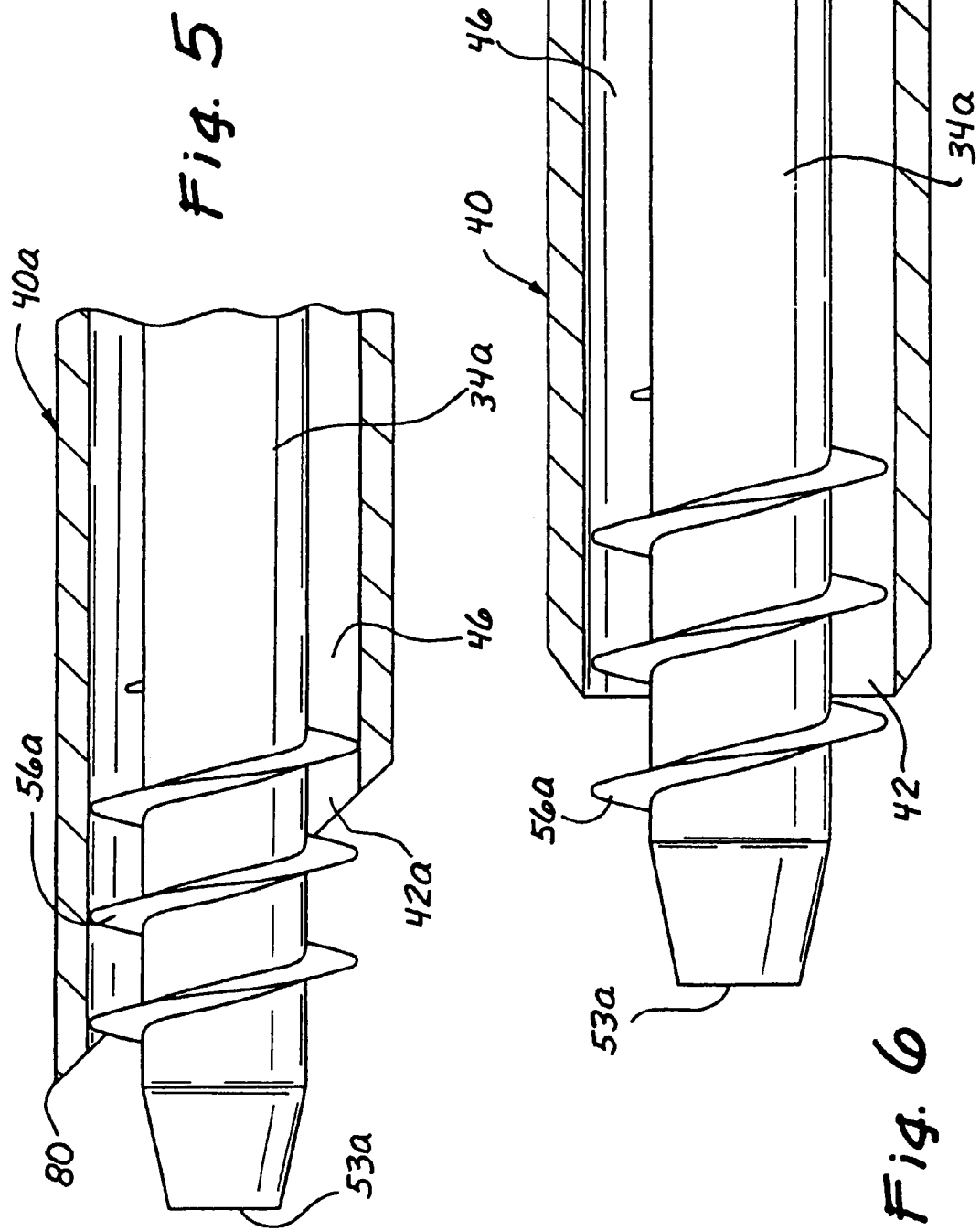

MICRO-INVASIVE DEVICE

RELATED APPLICATION

This application is a continuation of application Ser. No. 10/667,768, filed Sep. 22, 2003, which application is a continuation of Ser. No. 10/093,765, filed Mar. 8, 2002, which claims the benefit of U.S. provisional application Ser. No. 60/278,128, filed Mar. 23, 2001 and Ser. No. 60/281,848, filed Apr. 5, 2001 and Ser. No. 60/305,178 filed Jul. 13, 2001 and Ser. No. 60/322,909, filed Sep. 17, 2001 and Ser. No. 60/342,436, filed Dec. 21, 2001, the disclosure of each of which is incorporated in its entirety herein by reference.

FIELD OF THE INVENTION

The present invention relates generally to medical devices, and, more particularly, to micro-invasive devices and methods for removing breast tissue for biopsy and treatment.

BACKGROUND OF THE INVENTION

The medical industry is constantly evolving through the adaptation of improved pharmaceutical, biotechnology, and medical device products and procedures. Techniques and technologies are being developed to treat internal areas of the body through less invasive means.

It is often desirable and frequently necessary to remove a portion of tissue from humans and other animals, particularly in the diagnosis and treatment of patients with cancerous tumors, pre-malignant conditions and other diseases or disorders. Typically, in the case of cancer, when the physician establishes by means of procedures such as palpation, x-ray or ultrasound imaging that suspicious circumstances exist, a biopsy is performed to determine whether the cells are cancerous. Biopsy may be done by an open or percutaneous technique. Open biopsy removes the entire mass (excisional biopsy) or a part of the mass (incisional biopsy). Percutaneous biopsy, on the other hand, is usually done with a needle-like instrument and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section. The type of biopsy utilized depends in large part on circumstances present with respect to the patient and no single procedure is ideal for all cases. However, core biopsy is extremely useful in a number of conditions and continues to be used frequently by the medical profession.

To arrive at a definitive tissue diagnosis, intact tissue is needed from an organ or lesion within the body. In most instances, only part of the organ or lesion need be sampled. However, the portions of tissue obtained must be representative of the organ or lesion as a whole. In the past, to obtain tissue from organs or lesions within the body, surgery had to be performed to locate, identify and remove the tissue. With the advent of medical imaging equipment (x-rays and fluoroscopy, computed tomography, ultrasound, nuclear medicine, and magnetic resonance imaging) it has become possible to identify small abnormalities even deep within the body. However, definitive tissue characterization still requires obtaining adequate tissue samples to characterize the histology of the organ or lesion. For example, mammography can identify non-palpable (not perceptible by touch) breast abnormalities earlier than they can be diagnosed by physical examination. Most non-palpable breast abnormalities are benign; some of them are malignant. When breast cancer is diagnosed before it becomes palpable, breast cancer mortality can be reduced. However, it is often difficult to determine if pre-palpable breast abnormalities are malignant, as some benign lesions have mammographic features which mimic malignant lesions and some malignant lesions have mammographic features which mimic benign lesions. Thus, mammography has its limitations. To reach a definitive diagnosis, tissue from within the breast must be removed and examined under a microscope. Early biopsy techniques for reaching a definitive tissue diagnosis for non-palpable breast disease required a mammographically guided localization, either with a wire device, visible dye, or carbon particles, followed by an open, surgical biopsy utilizing one of these guidance methods to lead the surgeon to the non-palpable lesion within the breast.

Open surgical breast biopsies have many drawbacks. They can be disfiguring, expensive and are imperfect. Open surgical biopsies also carry a small mortality risk (due to the risks of anesthesia) and a moderate morbidity rate (including bleeding, infection, and fracture or migration of the localizing wire). In cases where multiple lesions are present in the breast, a surgeon is reluctant to biopsy each lesion due to the large tissue mass that must be extracted with each lesion. The most convenient lesion may be taken which most often results in an incomplete diagnosis.

Percutaneous breast biopsy techniques are more desirable in many instances, particularly in light of modern imaging techniques which are able to pinpoint non-palpable tissue masses in the breast and consequently, the increased frequency of biopsies that are necessary for diagnosis of these tissue masses. A well known instrument used quite extensively for core biopsies in the past is manufactured by Travenol Laboratories of Deerfield, Ill., and is sold under the mark "TRU-CUT." This manual biopsy instrument at one time enjoyed as much as 98% of the market for such devices. As disclosed in U.S. Pat. No. 3,477,423, the instrument comprises a two-piece assembly: an outer cutting cannula mounted to one hub member and an inner stylet with a sampling notch ground into it mounted to a second hub, with the hubs being slidably interlocked. The instrument is assembled and placed into the body with the outer cutting cannula just to the rear of a lancet point or beveled distal end of the stylet. Upon inserting the device up to or in front of the area to be biopsied, advancement of the assembly is halted. The stylet is manually advanced distally of the cannula with the cannula held stationery. Upon advancement of the stylet, the specimen notch is exposed. Tissue surrounding the stylet prolapses into the specimen notch and the cutting cannula is then manually advanced distally over the stylet, slowly shearing off the tissue entrapped in the stylet's specimen notch. The instrument is then either (a) withdrawn and the stylet advanced distally to expose the tissue for preparation for study or (b) left in place and only the stylet is proximally removed from within the cannula so a determination of successful sampling may be made. If the sampling was not successful, the stylet may be reinserted into the cannula, which remains positioned within the patient, and an attempt to reposition the assembly of stylet and cannula and repeat sampling can be made.

Such a technique using this basic design of a biopsy instrument is referred to as a manual technique. One drawback to the manual technique is that it requires a great deal of manual dexterity and motor coordination, along with the use of both hands, to advance the stylet while maintaining the position of the cannula and then to maintain the position of the stylet while advancing the cannula. Another drawback is that the cannula is advanced relatively slowly, resulting in an extremely poor cutting action and allowing the surrounding tissue an opportunity to collapse, thus making no use of the stored kinetic energy in the material being severed. Further disadvantages are encountered when the tissue volume to be sampled contains areas of higher density than that of surrounding tissue, such as areas of calcification commonly associated with certain types of cancerous growths. A manually inserted sampling device is often incapable of penetrating the denser area of tissue which merely deflects the course of the cannula/stylet structure around the dense area and into the more compliant surrounding tissue. In the late 1980's, two different stereotactic guidance systems were modified to allow the guiding portion of each system to accommodate spring powered devices such as the Biopty® (Bard Radiology) gun. As used herein, the term "gun" is used to refer to a tissue sampling device designed for "one-handed" operation. A feature common to many of these devices is the shape of the device being adapted to fit the hand of a medical practitioner with a pistol-like grip, complete with a triggering mechanism. Free-hand ultrasound guidance techniques were also developed to guide the Biopty® gun to breast lesions detected by ultrasound.

With image-guided percutaneous core breast biopsy, it should be possible to greatly reduce the number of open, surgical breast biopsies performed. However, there are limiting factors with image-guided breast biopsies. Conventional, manually operated two-step devices are awkward to manipulate, and the tissue samples obtained thereby are often unsatisfactory.

A variety of automatic and semiautomatic biopsy instruments have been developed which are spring loaded gun-type devices. A biopsy gun currently used is described in U.S. Pat. No. Re. 34,056, entitled "TISSUE SAMPLING DEVICE," issued to Lindgren et al. Additional examples of biopsy gun devices are disclosed in U.S. Pat. Nos. 4,600,014 and 4,958,625.

Such devices use a design comprising a handle held in a physician's palm, and a guide tube extending forwardly of the handle. A cannula is slidably disposed within the guide tube and is movable from within the guide tube forwardly out of the distal end of the guide tube. A sampling stylet is telescopically disposed within the cannula and projects from the rear of the handle. In an automatic mode of operation, the cannula, when in the retracted position, is spring loaded by means of a compressed spring. A release lever, which works against the compressed spring, is activated to release compression of the spring which then expands and pushes the cannula outwardly over the stylet. This instrument, as stated, requires two handed operation. Also, since the stylet is not removable proximally from within the handle, the entire instrument must be withdrawn to obtain access to the sample.

A fully automatic instrument manufactured by Radiplast, Inc. of Sweden is described in U.S. Pat. No. 4,699,154. This instrument comprises a reusable, spring-loaded box-shaped housing or handpiece, which activates a disposable cannula and stylet set. Both the stylet and cannula are activated in rapid succession. The instrument has the advantage of reducing the dexterity and motor coordination necessary in the use of manual devices and also eliminates the slow cutting action of the manually advanced cannula, replacing it with a very quick, clean cut. This instrument, however, also has its drawbacks. First, the reusable handpiece is very large, heavy, cumbersome, and expensive. They are also typically spring-powered devices and must be manually cocked with some sort of plunger bar. Such "cocking" of the gun requires considerable force and the gun must be cocked for each biopsy cut. When actuated, the springs provided in the gun accelerate the needles until a mechanical stop position is reached which can create a loud snapping noise and jerking motion which is a problem both to the physician and the patient. A further drawback is encountered in automatically activating both the stylet and the cannula, as opposed to activating the stylet manually, in that the rapid speed at which the cannula follows the stylet into the tissue does not allow much tissue to collapse into the specimen notch, limiting the size of the sample.

U.S. Pat. No. 5,183,054, entitled "ACTUATED BIOPSY CUTTING NEEDLE WITH REMOVABLE STYLET," issued to Burkholder et al., discloses a biopsy device having a tubular cannula through which a stylet, having a stylet cavity near the distal end, is placed. The stylet is removable from the cannula and removed from the biopsy device through the housing so that the tissue sample obtained by the biopsy device may be manually retrieved while the cannula remains in place within the patient, near the area being sampled. Thereafter, the stylet may be reinserted through the housing and cannula into the patient's tissue where additional tissue samples may be obtained. In this way, trauma to the tissue that ordinarily occurs upon reinsertion of the cannula and stylet is minimized.

U.S. Pat. No. 5,234,000, entitled "AUTOMATIC BIOPSY DEVICE HOUSING A PLURALITY OF STYLETS," issued to Hakky et al. describes a biopsy device for taking a plurality of samples of tissue from a living being. The device comprises a housing having a portion arranged to be held by a person using the device, a cannula having a proximal portion and a distal portion and being coupled to the housing. A plurality of stylets are located in the housing, with each of the stylets having a proximal end, a distal end, and a tissue receiving notch located adjacent the distal end. Each stylet is individually propelled through the cannula into the body so that a portion of the tissue prolapses into the notch.

There currently exists a need for a more effective microsurgical device for obtaining a sample of breast tissue from a patient.

SUMMARY OF THE INVENTION

New apparatus and methods for removing breast tissue and/or other material from a human breast have been discovered. The present invention provides apparatus, for example, micro-invasive apparatus, to remove tissue or other material from a target area of a breast to provide one or more benefits, such as diagnostic benefits, therapeutic benefits and the like.

The apparatus of the invention are useful for removing unwanted, diseased, or even healthy bodily materials, for example, tissues, for medical treatment and/or therapeutic purposes. Advantageously, the present invention is suitable for use in many surgical settings and is suitable for performing various material removal procedures using methodologies, for example, in terms of methods of introducing the apparatus into the body and removing the apparatus from the body, which are substantially analogous to conventional surgical techniques. Necessary or desirable adaptations of the apparatus of the present invention for specific medical treatment, e.g., diagnostic, and therapeutic purposes will be readily appreciated by those of skill in the art.

Accordingly, apparatus for removing tissue from a target area of a breast are provided. In one broad aspect, the apparatus comprise a handpiece and a tissue removal element connected or coupled thereto. The tissue removal element includes a cannula, for example, a substantially rigid or flexible cannula, and a rotational element disposed in the cannula. The rotational element is connected to a source of rotational energy, for example, a motor. The rotational element is disposed at least partially in the cannula. The cannula includes an open distal tip structured to be placed in a breast, and preferably a proximal end connected, for example, removably connected, to the handpiece. The tissue removal element is structured and effective to draw breast tissue or other material from the target area or site, for example, into the open distal tip, in response to, for example, as a result of, rotation of the rotational element relative to the cannula.

In one embodiment, the rotational element is structured to at least assist in drawing material from a breast into the cannula. For example, the rotational element and the cannula cooperatively engage to form or create a source of suction sufficient to draw the tissue or other material into the cannula in response to rotation of the rotational element relative to the cannula. Advantageously, the cannula, in particular the interior hollow space formed or defined by the cannula, and the rotational element are sized and positioned, relative to each other, to create a source of suction or pumping action in response to the rotational element rotating relative to the cannula. Without wishing to limit the invention to any particular theory of operation, it is believed that this functioning of the cannula/rotational element combination is at least somewhat analogous to the functioning of a pump, for example, a pump based on the principles of the "Archimedes' screw", causing the material to be drawn or pulled or pumped into the open distal tip of the cannula and through the cannula in being removed from the target area of the human/animal body.

Preferably, the suction/pumping action created or formed by the cannula/rotational element combination is itself sufficient and effective so that no other, for example, no additional or supplemental, source of suction or pumping action is employed, needed or required to effectively remove material from the target area in accordance with the present invention.

In one embodiment of the invention, the rotational element includes a shaft and one or more outwardly extending projections, for example threads, preferably having a substantially helical configuration. Advantageously, the rotational element includes a distal portion with such projections or threads. The proximal portion of the rotational element may or may not include such projections or threads. In a very useful embodiment, the proximal portion is substantially free of such projections or threads.

The distal portion of the rotational element, in a useful embodiment, extends beyond the open distal tip or inlet of the cannula, for example, by a distance in a range of about 0.02 inches to about 1 inch beyond the open distal tip of the cannula. For example, the distal portion may extend a distance equal to at least about one-half of the spacing between adjacent projections or threads. The rotational element distal portion may extend a distance equal to more than about one spacing, for example, about two spacings or more between adjacent projections or threads beyond the open distal tip of the cannula. More specifically, the rotational element advantageously further includes an elongated shaft having a proximal portion which is substantially smooth to allow sufficient annular space between the shaft and cannula for removal of material.

The cannula may be of any suitable size. However, in order to obtain the reduced invasiveness benefits of the present invention, it is preferred that the cannula size have an outer diameter of no greater than about 5 mm and more preferably about 2.0 mm or smaller.

It has unexpectedly been found that the present apparatus including such small size cannulas not only provide for reduced, or even micro, invasive procedures (which reduce surgical trauma and promote healing) but also are effective in removing materials from a body to achieve therapeutic benefits, for example, therapeutic removal of healthy or diseased breast tissue, fluidic cystic materials, soft tissue tumors, and the like.

In one embodiment of the invention, the open distal tip of the cannula is angled or is beveled with respect to a longitudinal axis of the cannula. Alternatively, the open distal tip is substantially perpendicular with respect to the longitudinal axis of the cannula.

The present apparatus advantageously includes a tissue collection chamber in communication, for example, fluid communication, with the cannula and structured to collect and contain material, for example breast tissue, that is passed through the cannula. The collection chamber preferably is structured to facilitate quantification and/or other analysis of the removed material. In one particularly useful embodiment, the collection chamber comprises a substantially transparent conical section removably engaged to a housing of the handpiece and preferably circumscribing a portion, for example, the proximal portion of the shaft of the rotational element.

The cannula and/or the rotation element, preferably both, advantageously are structured to be manually deformable, for example, to enable the physician to alter the normal configuration, for example, the normal substantially straight configuration, thereof to create a curved configuration if desired, for example, to deal with the material removal application at hand.

In another broad aspect of the present invention, methods of removing material from a breast of a human or an animal are provided. Such methods comprise placing into a breast of a human or an animal a cannula having an open distal tip and a rotational element disposed at least partially in the cannula and rotating the rotational element relative to the cannula, thereby at least assisting in drawing a material from the breast into the open distal tip of the cannula. The method preferably further comprises passing the material from the breast through the cannula. Apparatus in accordance with the present invention described herein, can be advantageously employed in accordance with the present methods.

The cannula used in accordance with the present methods preferably have outer diameters of about 5 mm or less, or about 2.0 mm or less.

The placing step of the present methods preferably includes percutaneously introducing the cannula into the human or animal breast, and positioning the open distal tip of the cannula in close proximity to the material to be removed. The cannula and rotational element preferably are sized and positioned relative to each other so that the rotating step is effective in drawing the material from the breast of a human or an animal into the open distal tip of the cannula. Preferably, the material from the breast is removed without applying additional suction or aspiration to the open distal tip of the cannula.

In one very useful embodiment, the rotating of the rotational element relative to the cannula is effective to draw the material into the cannula as a substantially single, continuous often times substantially cohesive piece. Thus, although some shearing and/or cutting of the material to be removed may occur in accordance with the present invention, for example, so that the removed material is compatible with the space within the cannula through which the material is to be moved proximally, the present apparatus and methods preferably are not based on cutting or chopping the material to be removed into small discrete segments.

The present methods preferably further comprise collecting the material removed and/or observing and/or otherwise testing the material removed.

Any suitable material can be removed from the body of a human or an animal using the present apparatus and/or methods. Preferably, such material to be removed can be effectively removed using the present apparatus and/or methods without employing or requiring additional suction or aspiration, beyond that formed or created by the rotation of the rotational element relative to the cannula.

Advantageously, the material to be removed is soft and/or semi-solid and/or a viscous flowable material and/or a material which is at least somewhat free to move toward a source of lower pressure or suction.

Incorporated herein by this specific reference are U.S. patent application for Micro-invasive Tissue Removal Device, having Ser. No. 10/093,775, filed on Mar. 8, 2002, and commonly assigned herewith, and U.S. patent application for Micro-invasive Nucleotomy Device and Method, having Ser. No. 10/093,774 filed on Mar. 8, 2002, and commonly assigned herewith.

Each and every feature described herein, and each and every combination of two or more of such features, is included within the scope of the present invention provided that the features included in such a combination are not mutually inconsistent.

The present invention and the objects and advantages thereof will be more clearly understood and appreciated with respect to the following Detailed Description, when considered in conjunction with the accompanying Drawings.

BRIEF DESCRIPTION OF THE DRAWINGS

FIG. 1 shows a side view of a micro-invasive breast tissue removal apparatus in accordance with the present invention including a handpiece and a tissue removal element connected thereto.

FIG. 2 is a partial cross-sectional view of the apparatus taken along line 2-2 of FIG. 1.

FIG. 3 is a partial cross-sectional view of a preferred distal tip of the tissue removal element of the apparatus in accordance with the present invention.

FIG. 4 is side view of the apparatus shown in FIG. 1, with the tissue removal element having a curve for facilitating access to breast tissue.

FIGS. 5 and 6 each show a partial cross-sectional view of an alternative distal tip of the tissue removal apparatus of the present invention.

DETAILED DESCRIPTION

Turning now to FIGS. 1 and 2, a micro-invasive tissue removal apparatus for removing tissue or other material from a breast, in accordance with the present invention is shown generally at 10. The apparatus 10 generally comprises a handpiece 14 and a tissue removal mechanism 16 to be described in detail hereinafter.

The handpiece 14 is preferably sized and contoured to fit comfortably within a palm of a surgeon, and includes, for example, a molded plastic housing 22. As shown in FIG. 2, the housing 22 of the handpiece 14 encloses a small motor 24 and a power supply, for example, a 9 volt battery 26 for driving the tissue removal mechanism 16. Suitable electrical connectors 27 are provided. For convenient, one handed operation, an ON/OFF switch 28 is preferably provided on a recessed, lateral portion 29 of the housing 22.

Turning now as well to FIG. 3, the tissue removal mechanism 16 generally includes a cannula 30 and a rotatable element 34 disposed therein. As shown most clearly in FIG. 3, the cannula 30 includes a distal portion 40 defining an inlet 42 for receiving tissue drawn from a target area within a patient. The inlet 42 is defined, for example, by flat, distal edge 44 of the cannula 30. The distal edge 44, in the embodiment shown in FIG. 3, lies along a plane that is substantially perpendicular with respect to the longitudinal axis of the cannula 30. During operation of the apparatus 10, as will be described in greater detail hereinafter, breast tissue and/or other material is drawn, suctioned or pumped, through the inlet 42 and into a cylindrical bore 46 defined between the cannula 30 and a shaft 50 of the rotatable element 34.

In a preferred embodiment of the invention, such as shown in FIGS. 1-3, the tissue removal mechanism 16 is structured to draw breast tissue or other material into the cannula 30 by a pumping action produced by rotation of the rotatable element 34, preferably without the use of supplemental aspiration or other means for drawing tissue into the threaded distal portion 52 or cannula 30. In other words, the rotational element 34 and the cannula 30 are designed to cooperatively engage to form a source of suction that is, in itself, sufficient to draw the material into the cannula 30. Advantageously, the present invention 10 has been found to be safe and highly effective for removing soft tissues from a breast of a patient, for example, less invasively, without being connected to external sources of aspiration or other external machines and devices. In the preferred embodiment of the invention, the rotational element 34 includes a distal portion 52 which extends beyond the open distal tip (defined by edge 44) of the cannula 30. More preferably, the distal portion 52 extends a length of about 0.066 inches beyond the cannula distal edge 44. A blunt, rounded tip 53 of the rotational element 34 is preferably provided.

As shown, the rotational element 34 includes one or more outwardly extending projections, for example threads such as helical threading 56 shown, disposed about at least a portion of the shaft 50, for urging tissue into the bore 46. Preferably, outer radial edge 58 of the threading 56, or other projection, is disposed closely proximate an inner wall 62 of the cannula. As shown, the distal end 52 of the rotational element 34 extends at least one-half thread turn beyond the cannula inlet 42. This structure allows breast tissue or other material within the breast to prolapse between the outer, distal-most threading turns, and be pulled into the inlet without necessarily being discretely cut or severed by the threading 56. The present invention is designed such that upon insertion of the open distal tip of the cannula 30 into the target region of the breast of a body, tissue or other material will prolapse into and at least partially fill the open spaces between the projections or threading 56. Rotation of the rotational element 34, for example, at about 12,000 RPM, causes the material to be pulled in a proximal direction proximally into the bore 46, for example, as a continuous piece or strand of material.

Although the threading 56 is only shown as a single thread located on the distal portion 52 of the rotational element 34, it is to be appreciated that in some embodiments of the invention, the threading 56 may involve multiple threads, and/or may be disposed on more proximally located portions of the rotatable element shaft 50. Furthermore, although only about 4.5 turns of threading 56 are shown, it is to be appreciated that in some embodiments of the present invention, fewer or more than 4.5 turns of threading 56 may be provided. It is also contemplated by the present invention that rather than continuous threading 56, the shaft 50 may be provided with discontinuous threading. It is contemplated that with appropriate modifications and the like, these and other structures may be provided which would operate in a manner similar to the pumping action provided by the structure shown.

Preferably, the cannula 30 has an outer diameter of less than about 5 mm, for example, an outer diameter of about 2.0 mm or less. The cannula 30 is made of any suitable, medical grade material or materials, but is preferably somewhat rigid but bendable.

Advantageously, as will be appreciated by those of skill in the art, the apparatus 10 of the present invention is minimally invasive to the patient. For example, the cannula 30 can be introduced into the target area of the breast of the patient by means of a conventional, rigid stylet (not shown) disposed through the cannula 30 (detached from the handpiece 14). The cannula/stylet are introduced percutaneously through the skin, underlying muscle/fatty tissue and into the target area within or adjacent a breast such that the inlet 42 is positioned within or closely adjacent the target tissue or other material. The stylet is then removed and the cannula 30 is left in place. The rotational element 34, attached to the handpiece 14, is then introduced into the cannula 30. This procedure may be facilitated through the use of fluoroscopy or x-ray imaging techniques as known in the art, which do not require direct endoscopic or direct viewing of the target tissue.

Advantageously, unlike prior art surgical breast tissue removal devices, the action of the tissue removal mechanism 16 urges tissue into the cannula 30 in many instances a substantially continuous segment rather than in relatively smaller, distinct portions of the tissue. Generally, the cannula 30 and rotational element 34 are structured to cooperatively function in a manner that will form a source of suction within the cannula 30 when the rotational element 34 is rotated while the cannula inlet 42 is disposed within the target tissue. It has been found that the level of suction so created is sufficient to gently and effectively draw soft tissue, for example, gelatinous, viscous, or any suitable tissue that can be drawn by the action of the present invention into the cannula without need for any other, for example, supplemental, source of suction applied to the inlet 42. For example, the suction formed or created is sufficient to pull or soft tissues into the open tip without causing damage to other structures.

The tissue removal mechanism 16 can be left to remain in substantially the same position within the target area of the breast during the tissue removal procedure, or alternatively may be advanced, or withdrawn during the procedure, for example in a direction along the longitudinal axis of the cannula in order to facilitate tissue removal.

FIG. 4 shows another advantageous feature of the present invention. The tissue removal mechanism 16 may be structured to be deformed, for example, manually deformed, into a curve shape such as shown. The flexibility and deformability of the tissue removal mechanism 16 allows custom shaping or curving of the apparatus 10 for further facilitating access to tissue.

Unlike prior art devices designed to remove substantially liquid substances, the present invention can be used to remove highly viscous substances.

FIG. 5 shows an alternative cannula distal portion 40a, which is beveled, includes sharp distal tip 80, and a relatively wider inlet 42a than inlet 42. Also shown is a narrower threading 56a (relative to threading 56 of FIG. 3) on rotational element 34a. It is contemplated that in some embodiments of the present invention, a beveled cannula may be provided (such as in FIG. 5) and the rotational element may be somewhat recessed within the cannula, in that it does not extend further than a distal-most tip 80 thereof. Thus, it is contemplated that as long as at least a portion of threading is exposed to tissue through the angled inlet, the tissue will be drawn into the inlet 42a and effectively removed upon rotation of the rotatable element.

FIG. 6 shows a cannula distal portion 40 similar to that shown in FIG. 3. However the rotational element 34a is similar to that shown in FIG. 5, having narrow helical threading 56a, and a flat tip 53a rather than the rounded tip 53 shown in FIG. 3.

As shown in FIGS. 1, 2 and 4, the apparatus 10 may further comprise a collection chamber 70, for example, defined by a subhousing 72 removably engaged to the housing 22. More specifically, the collection chamber 72 is in fluid communication with a proximal portion 76 of the cannula 30. For example, the collection chamber 70 is adapted to collect, temporarily contain, and allow analysis of breast tissue or other material, for example during and/or after the tissue removal procedure.

Generally, the collection chamber 70 is structured to contain material that is drawn from the surgical site. The removed material enters the collection chamber 70 as shown by arrows 74 in FIG. 2. The collection chamber 70 is preferably adapted to allow observation of the tissue material during the procedure. For example, the subhousing 72 may be transparent. In addition, the collection chamber 70 is preferably structured to allow quantification or measurement of the tissue, for example, the subhousing 72 may be provided with suitable indices (not shown) showing milliliters (ml) of material collected therein. After the tissue removal procedure, the breast tissue may be biopsied using conventional means. As shown, a proximal portion 78 of the rotatable element 34 is circumscribed by the collection chamber 70.

It is further contemplated that in many applications of the present invention, the cannula 30 may alternatively or additionally be used as a passageway for introducing medication and other agents into the target region of the breast before or after the tissue removal, if desirable.

It can be appreciated that the present apparatus is less invasive and more passive in comparison to other percutaneous breast tissue removal devices in the art. Despite its simplicity and passivity, the present device is designed to be highly effective in removing soft tissue, for example, cystic materials, fatty tissue, and muscle tissue or other materials that may be found in the breast. Because there is no external suction source or supplemental aspiration required to pull material into the cannula, it can further be appreciated that the apparatus is smaller, safer and requires less monitoring than devices that include a separate or external source of suction or additional idler shafts for removing material.

It is also to be appreciated that the apparatus of the present invention may be modified to include a connector for enabling the handpiece to be connected to an external aspiration source. In this case, means for monitoring the vacuum level in the cannula is preferably provided in order to indicate and prevent build-up of excess vacuum in the event the cannula becomes clogged for example.

While this invention has been described with respect to various specific examples and embodiments, it is to be understood that the invention is not limited thereto and that it can be variously practiced within the scope of the following claims.

What is claimed is:

1. A self-contained apparatus for removing a gelatinous substance from a target area of a human body, the apparatus comprising:
   a handpiece;
   a source of rotational energy;
   a cannula including a proximal end portion structured to be coupled to the handpiece and an open distal tip adapted to be placed in the target area of the human body prior to the proximal end portion being coupled to the handpiece;

a rotational element structured to be operatively coupled to the source of rotational energy, the rotational element disposed at least partially in the cannula, wherein the apparatus is structured so that the rotational element and the cannula cooperatively engage to form a source of suction effective in drawing a gelatinous substance from the target area of the human body into the cannula in response to rotation of the rotational element; and the apparatus including no external source of suction and being structured to be self-contained.

2. The self-contained apparatus of claim 1, wherein the handpiece is sized and contoured to fit comfortably within a palm of a surgeon.

3. The self-contained apparatus of claim 1, wherein the cannula is sized and structured to be rigid and manually deformable.

4. The self-contained apparatus of claim 3, wherein the cannula and the rotational element are manually deformable into a desired curved shape.

5. The self-contained apparatus of claim 1, wherein the source of rotational energy comprises a motor.

6. The self-contained apparatus of claim 1, wherein the cannula has an outer diameter no greater than about 5 mm.

7. The self-contained apparatus of claim 1, wherein the rotational element is structured to rotate at a sufficiently high speed to cause the gelatinous substance from the target area of a human body to be pulled proximally into the cannula.

8. The self-contained apparatus of claim 1, wherein the source of rotational energy is a source of battery-powered rotational energy.

9. The self-contained apparatus of claim 8 which further comprises a battery coupled to and effective to provide power to the source of battery-powered rotational energy.

10. A self-contained apparatus for removing a gelatinous substance from a target area of a human body, the apparatus comprising:
 a handpiece;
 a source of rotational energy;
 a cannula including a proximal end portion structured to be coupled to the handpiece and an open distal tip adapted to be placed in the target area of the human body;
 a rotational element structured to be introduced into the cannula and the target area of the human body after the open distal tip is placed in the target area of the human body and to be operatively coupled to the source of rotational energy, wherein the apparatus is structured so that the cannula and the rotational element disposed at least partially in the cannula cooperatively engage to form a source of suction effective in drawing a gelatinous substance from the target area of the human body into the cannula in response to rotation of the rotational element; and
 the apparatus including no external source of suction and being structured to be self-contained.

11. The self-contained apparatus of claim 10, wherein the source of rotational energy comprises a motor.

12. The self-contained apparatus of claim 10, wherein the cannula has an outer diameter no greater than about 5 mm.

13. The self-contained apparatus of claim 10, wherein the rotational element is structured to rotate at a sufficiently high speed to cause the gelatinous substance from the target area of a human body to be pulled proximally into the cannula.

14. The self-contained apparatus of claim 10, wherein the source of rotational energy is a source of battery-powered rotational energy.

15. The self-contained apparatus of claim 14 which further comprises a battery coupled to and effective to provide power to the source of battery-powered rotational energy.

16. A self-contained apparatus for removing a gelatinous substance from a target area of a human body, the apparatus comprising:
 a handpiece;
 a source of rotational energy;
 a cannula including a proximal end portion structured to be coupled to the handpiece and an open distal tip adapted to be placed in the target area of the human body;
 a rotational element structured to be operatively coupled to the source of rotational energy, the rotational element disposed at least partially in the cannula and extending beyond the distal tip of the cannula, wherein the apparatus is structured so that the rotational element and the cannula form a source of suction effective in drawing a gelatinous substance from the target area of the human body into the cannula in response to rotation of the rotational element; and
 the apparatus including no external source of suction.

17. The self-contained apparatus of claim 16, wherein the rotational element is structured to rotate at a sufficiently high speed to cause the gelatinous substance from the target area of the human body to be pulled proximally into the cannula.

* * * * *

UNITED STATES PATENT AND TRADEMARK OFFICE
CERTIFICATE OF CORRECTION

PATENT NO. : 7,591,790 B2
APPLICATION NO. : 11/888321
DATED : September 22, 2009
INVENTOR(S) : Pflueger Page 1 of 1

It is certified that error appears in the above-identified patent and that said Letters Patent is hereby corrected as shown below:

Column 9

Line 40, "pull or soft" should read --pull soft--.

Signed and Sealed this

Twenty-second Day of December, 2009

David J. Kappos
*Director of the United States Patent and Trademark Office*